United States Patent [19]
Dow et al.

[11] Patent Number: 5,593,997
[45] Date of Patent: Jan. 14, 1997

[54] 4-AMINOPYRAZOLO(3-,4-D)PYRIMIDINE AND 4-AMINOPYRAZOLO-(3,4-D)PYRIDINE TYROSINE KINASE INHIBITORS

[75] Inventors: Robert L. Dow; Kevin Koch; Gary R. Schulte, all of Groton, Conn.

[73] Assignee: Pfizer Inc., New York, N.Y.

[21] Appl. No.: 449,381

[22] Filed: May 23, 1995

[51] Int. Cl.$^6$ .................. C07D 239/70; A61K 31/415
[52] U.S. Cl. ............................. 514/258; 544/262
[58] Field of Search ................. 544/262; 514/258

[56] References Cited

U.S. PATENT DOCUMENTS 4,044,130  8/1977  Howarth et al. ............ 424/248.56

FOREIGN PATENT DOCUMENTS

WO9413677  11/1993  WIPO .

OTHER PUBLICATIONS

Tominaga, Y, "Synthesis . . . ", Journal of Heterocylic Chem., 27, 647–60, (1989).
Gatta, F., "Pyrazolo . . . ", J. Heterocyclic Chem., 26, 613 (1989).
Tominaga, Y, "Synthesis . . . ", Journal of Heterocyclic Chem., 27, 647–60, (1989).

*Primary Examiner*—Mukund J. Shah
*Assistant Examiner*—Anthony Bottino
*Attorney, Agent, or Firm*—Peter C. Richardson; Gregg C. Benson; A. Dean Olson

[57]      ABSTRACT

Certain 4-aminopyrazolo[3,4-d]pyrimidine compounds, and their pharmaceutically-acceptable salts and prodrugs, are inhibitors of tyrosine kinase enzymes and are useful for immunoregulation and for the treatment of cancer, angiogenesis and atherosclerosis.

16 Claims, No Drawings

4-AMINOPYRAZOLO(3-,4-D)PYRIMIDINE AND 4-AMINOPYRAZOLO-(3,4-D)PYRIDINE TYROSINE KINASE INHIBITORS

This invention relates to 4-aminopyrazolo-[3,4-d]pyrimidine and 4-aminopyrazolo[3,4-d]pyridine compounds which are tyrosine kinase inhibitors, pharmaceutical compositions containing such tyrosine kinase inhibitors, and the use of such tyrosine kinase inhibitors for the treatment of tyrosine kinase dependent diseases/conditions such as autoimmune diseases, graft rejection, cancer, angiogenesis or atherosclerosis, in mammals.

BACKGROUND OF THE INVENTION

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor, and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

For example, tyrosine kinase inhibitors are useful for inhibiting T-cell proliferation and thus they are useful as immunosuppressive agents for the prevention or treatment of graft rejection following transplant surgery and for the prevention or treatment of autoimmune diseases such as rheumatoid arthritis and psoriasis.

Graft or transplant rejection following transplant surgery is a common occurrence which arises when foreign antigens are recognized by the host's immune response system. Then, the host's immune response system, in an effort to "protect" itself from the foreign tissue, releases its arsenal of antibodies and soluble lymphokines which amplify the immunologic response. The antibodies attack the foreign tissue, resulting in complications which often end in rejection of said tissue.

Similarly, the occurrence of immunoregulatory irregularities in autoimmune and chronic inflammatory diseases is well known. Irrespective of the underlying etiology of the condition, a variety of autoantibodies and self-reactive lymphocytes often arise to complicate or perpetuate the condition.

Treatments which target the immune response system often result in a complete shutdown of the system, leading to a lowering of the body's ability to combat infection. This can be as dangerous as the original condition which led to the shutdown.

Currently the leading medicinal agent for the prevention or treatment of graft rejection is cyclosporin A, approved by the United States Food and Drug Administration in 1983. The drug acts by inhibiting the body's immune response system from mobilizing its arsenal of natural protecting agents to reject the transplant's foreign protein. Although cyclosporin is effective in fighting graft rejection, it suffers drawbacks in that it can cause kidney failure, liver damage and ulcers; which in many cases can be very severe. Safer drugs which are more selective in their ability to affect the immune response system and which have fewer side effects are constantly being pursued.

Thus, although there are a variety of therapies for treating tyrosine kinase dependent diseases there is a continuing need and a continuing search in this field of art for alternative therapies.

SUMMARY OF THE INVENTION

This invention is directed to compounds that are useful as tyrosine kinase inhibitors. The compounds of this invention have the Formula I

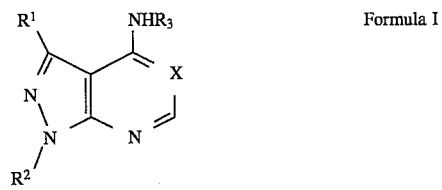

Formula I and the pharmaceutically-acceptable salts and prodrugs thereof wherein X is $C(R_4)$ or N;

$R_1$ is phenyl, mono-or di-halophenyl, mono-or di-alkoxy($C_1$–$C_4$)phenyl, mono- or di-alkyl($C_1$–$C_4$)phenyl, perhaloalkyl($C_1$–$C_4$)phenyl or nitrophenyl or said preceding $R_1$ groups mono-substituted on alkyl($C_1$–$C_4$) or $R_1$ ($C_1$–$C_6$)alkyl is pyrrolyl, imidazolyl, pyrazolyl, pyridyl, pyrimidinyl, pyrazinyl, pyridazinyl, furyl or thienyl;

$R_2$ is phenyl, mono-or di-halophenyl, mono-or di-alkoxy($C_1$–$C_4$)phenyl, mono- or di-alkyl($C_1$–$C_4$)phenyl, perhaloalkyl($C_1$–$C_4$)phenyl or nitrophenyl or said preceding $R_2$ groups mono-substituted on alkyl($C_1$–$C_4$) or $R_2$ is H, alkyl($C_1$–$C_6$), cycloalkyl($C_1$–$C_7$), pyridyl, halobenzoyl, alkoxy($C_1$–$C_4$)benzoyl, alkyl($C_1$–$C_4$)benzoyl, perhaloalkyl($C_1$–$C_4$)benzoyl, nitrobenzoyl, naphthyl, pyrrolyl, imidazolyl, pyrazolyl, pyridyl, pyrimidinyl, pyrazinyl, pyridazinyl, furyl or thienyl;

$R_3$ is H, alkyl($C_1$–$C_4$), morpholinoalkyl($C_1$–$C_4$), carboxyalkyl($C_1$–$C_3$) or alkoxy($C_1$–$C_4$)carbonylalkyl($C_1$–$C_3$); and $R_4$ is phenyl, halophenyl, alkoxy($C_1$–$C_4$)phenyl, alkyl($C_1$–$C_4$)phenyl, perhaloalkyl($C_1$–$C_4$)phenyl or said R, groups mono-substituted on alkyl($C_1$–$C_4$) or $R_4$ is cyano, H, halo, alkyl($C_1$–$C_6$), alkoxy($C_1$–$C_4$)carbonyl, alkanoyl($C_1$–$C_4$), carbamoyl, or alkyl($C_1$–$C_4$)carbamoyl.

A first group of preferred compounds of Formula I are those compounds wherein

X is N;

$R_1$ is phenyl, halophenyl, alkoxy($C_1$–$C_4$)phenyl, alkyl($C_1$–$C_4$)phenyl, perhaloalkyl($C_1$–$C_4$)phenyl or nitrophenyl;

$R_2$ is cyclohexyl, phenyl, halophenyl, alkoxy($C_1$–$C_4$)phenyl, alkyl($C_1$–$C_4$)phenyl, perhaloalkyl($C_1$–$C_4$)phenyl or nitrophenyl; and $R_3$ is H.

Within this first group of preferred compounds is a group of especially preferred compounds wherein $R_1$ is 4-methylphenyl or 4-chlorophenyl.

A second group of preferred compounds of Formula I are those compounds wherein

X is N;

$R_1$ is alkyl($C_1$–$C_4$)phenyl;

$R_2$ is phenyl; and $R_3$ is morpholinoalkyl($C_1$–$C_4$), carboxyalkyl($C_1$–$C_3$) or alkyoxy($C_1$–$C_4$)carbonylalkyl($C_1$–$C_3$).

Within this second group of preferred compounds of Formula I is a group of especially preferred compounds wherein $R_1$ is 4-methylphenyl.

A third group of preferred compounds of Formula I are those compounds wherein $R_3$ is H; and X is N.

Within this third group of preferred compounds of Formula I is a first group of especially preferred compounds wherein $R_1$ is alkyl($C_1$–$C_4$)phenyl or chlorophenyl; and $R_2$ is t-butyl or cyclohexyl.

Particularly preferred compounds within the above first group of especially preferred compounds wherein $R_1$ is chlorophenyl; and $R_2$ is cyclohexyl; or $R_1$ is chlorophenyl; and $R_2$ is t-butyl; or $R_1$ is 4-methylphenyl; and $R_2$ is cyclohexyl; or $R_1$ is 4-methylphenyl; and $R_2$ is t-butyl.

Within the third group of preferred compounds of Formula I is a second group of especially preferred compounds wherein $R_1$ is phenyl, alkyl($C_1$–$C_4$)phenyl, benzyl or alkyl($C_1$–$C_6$); and $R_2$ is H, pyridyl or alkyl($C_1$–$C_6$).

Particularly preferred compounds within the above second group of especially preferred compounds are compounds wherein $R_1$ is 4-methylphenyl; or $R_2$ is 2-pyridyl; or $R_1$ is 4-methylphenyl, benzyl or t-butyl; and $R_2$ is t-butyl.

A fourth group of preferred compounds of Formula I are those compounds wherein $R_1$ is phenyl;

$R_2$ is 3,4-dichlorophenyl, 1-naphthyl, phenyl, 4-nitrophenyl, 2-methylphenyl or 4-methoxyphenyl;

$R_3$ is H; and $R_4$ is N.

A fifth group of preferred compounds of Formula I are those compounds wherein $R_1$ is t-butyl or benzyl;

$R_2$ is phenyl;

$R_3$ is H; and $R_4$ is N.

A sixth group of preferred compounds of Formula I are those compounds wherein $R_1$ is 4-methylphenyl;

$R_2$ is benzyl or benzoyl;

$R_3$ is H; and $R_3$ is N.

The present invention is also directed to pharmaceutical compositions which comprise a therapeutically effective amount of a compound of Formula I and a pharmaceutically-acceptable carrier.

The present invention is also directed to pharmaceutical compositions which comprise a tyrosine kinase dependent disease or condition treating amount of a compound of Formula I and a pharmaceutically-acceptable carrier.

Yet another aspect of this invention is a method of treating a tyrosine kinase dependent disease or condition in a mammal which comprises administering to a mammal suffering from a tyrosine kinase dependent disease or condition, a tyrosine kinase dependent disease or condition treating amount of a compound of Formula I.

Tyrosine kinase dependent diseases or conditions refers to hyperproliferative disorders which are initiated/maintained by aberrant tyrosine kinase enzyme activity. Examples include psoriasis, cancer, immunoregulation (graft rejection), atherosclerosis, rheumatoid arthritis, angiogenesis (e.g., tumor growth, diabetic retinopathy), etc.

The term "treating" as used herein includes preventative (e.g., prophylactic) and paliative treatment.

By halo is meant chloro, bromo, iodo, or fluoro.

By alkyl is meant straight chain or branched saturated hydrocarbon.

As used herein, the expression "reaction-inert solvent" refers to a solvent which does not interact with starting materials, reagents, intermediates or products in a manner which adversely affects the yield of the desired product.

The chemist of ordinary skill will recognize that certain compounds of this invention will contain atoms which may be in a particular optical or geometric configuration. All such isomers are included in this invention.

The expression "pharmaceutically-acceptable salt" refers to nontoxic cationic and anionic (both inorganic and organic) salts. Exemplary anionic salts include chloride, bromide, iodide, sulfate, bisulfate, phosphate, acetate, maleate, fumarate, oxalate, lactate, tartrate, citrate, gluconate and 4-toluene-sulfonate. Exemplary cationic salts include sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

The expression "prodrug" refers to compounds which are drug precursors which, following administration and absorption, release the drug in vivo via some metabolic process. Exemplary prodrugs include acyl amides of the amino compounds of this invention such as amides of alkanoic($C_1$–$C_6$)acids, amides of aryl acids (e.g., benzoic acid) and alkane($C_1$–$C_6$)dioic acids.

Other features and advantages will be apparent from the specification and claims.

DETAILED DESCRIPTION OF THE INVENTION

In general the compounds of this invention in view of the disclosure herein can be made by processes, including processes known in the chemical arts. Certain processes for the manufacture of the compounds of this invention are provided as further features of the invention and are illustrated by the following reaction schemes.
REACTION SCHEME I
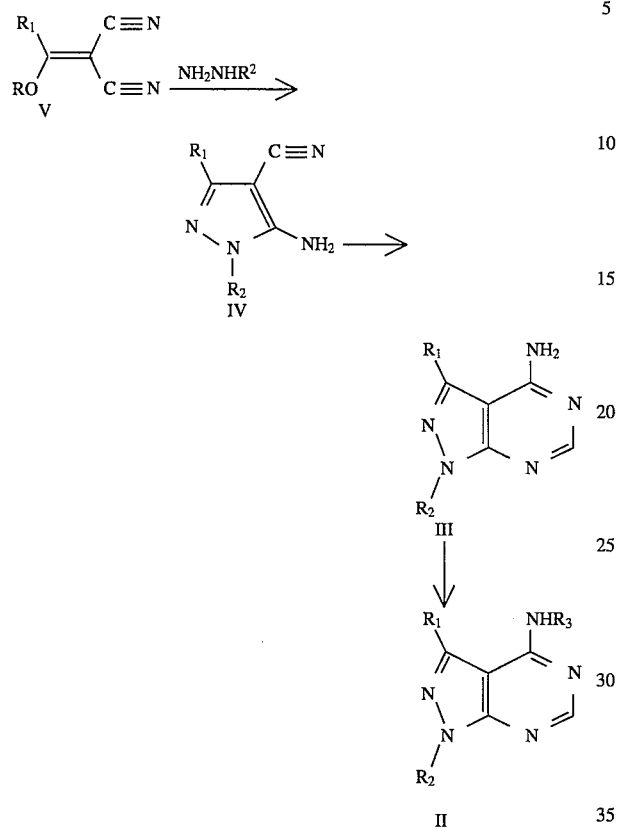
REACTION SCHEME II
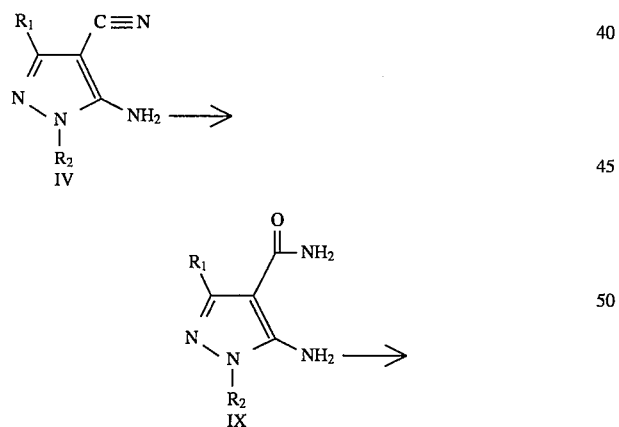
REACTION SCHEME II -continued
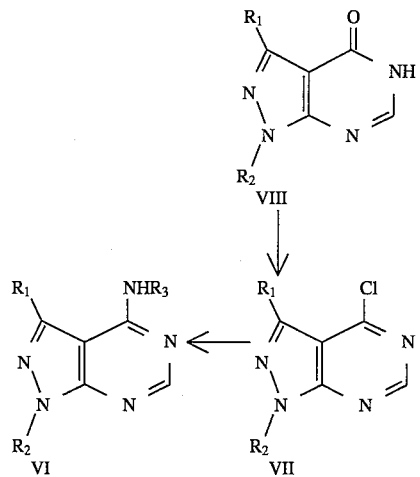

REACTION SCHEME III

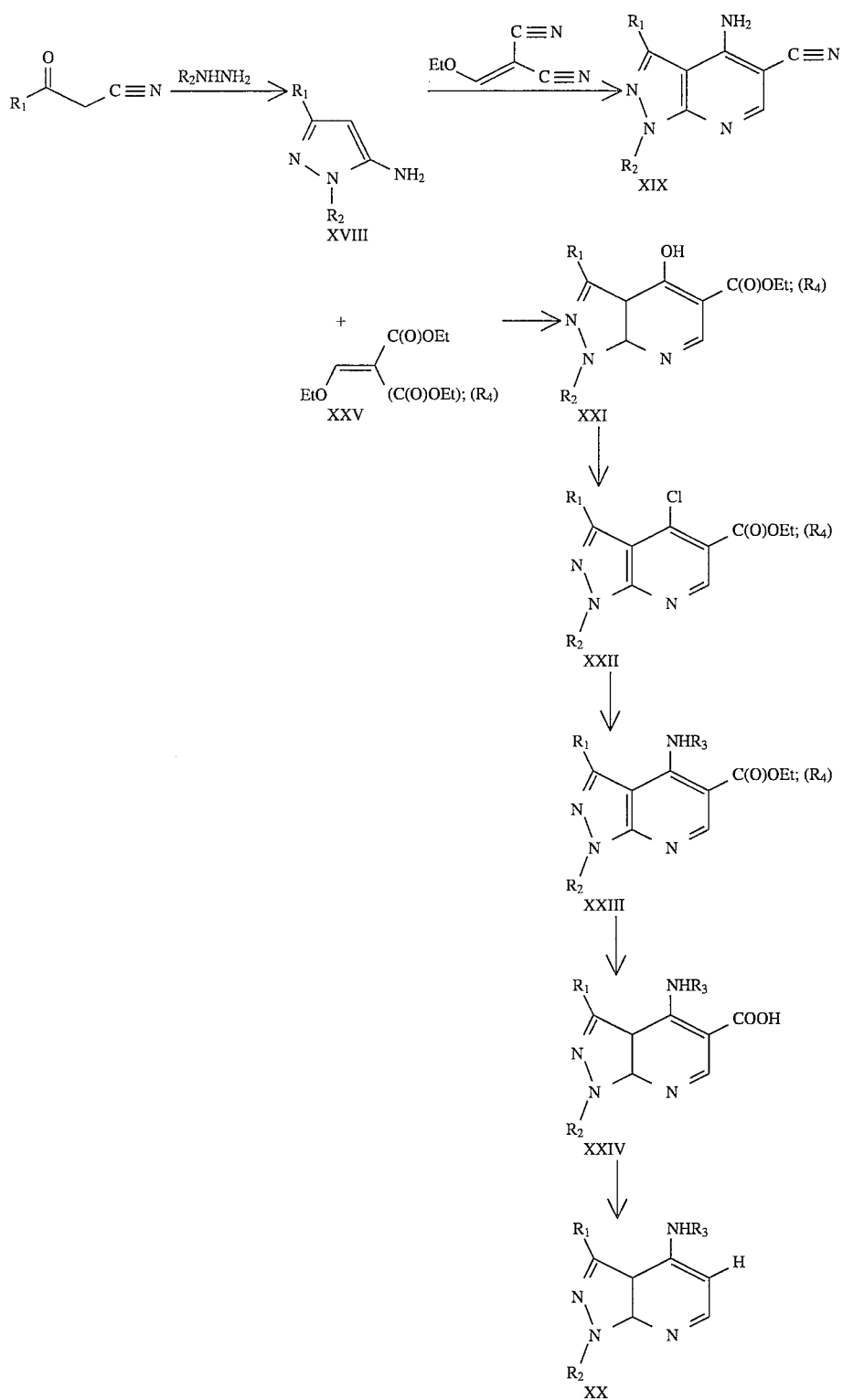

According to Reaction Scheme I Formula 1 compounds wherein X is N (i.e. Formula II compounds wherein $R_1$ is as defined above, $R_3$ is H and $R_2$ is acyl) may be prepared by acylating the appropriate Formula III compounds wherein $R_1$ is as defined above and $R_2$ is H.

Typically the Formula III compound is acylated with preferably one or less than one equivalent of the appropriate acid halide, preferably, in pyridine at 0° C. to 75° C. for 1 to 3 hours.

According to Reaction Scheme I compounds of the Formula I wherein $R_1$ is as defined above, $R_3$ is H and $R_2$ is as defined above (except for acyl) may be prepared by cyclizing the appropriate Formula IV compounds, wherein $R_1$ is as defined above and $R_2$ is as defined above except for acyl.

The Formula IV compound may be heated neat in formamide at a temperature of 150° C. to 220° C. for about 6 to about 24 hours. Alternatively, the Formula IV compound may be heated at 150° C. to 220° C. with formamide and a low molecular weight acid such as formic acid, in a polar aprotic solvent such as dimethylformamide (DMF), dimethylsulfoxide (DMSO) or 1-methyl-2-pyrrolidinone for about 6 to about 24 hours.

According to Reaction Scheme I the Formula IV compounds, wherein $R_1$ and $R_2$ are as defined above except $R_2$ is not acyl may be prepared by condensation of the appropriate hydrazine (containing $R_2$ as defined above except for acyl) with the appropriate Formula V compound wherein $R_1$ is as defined above and R is a conventional leaving group. Generally the Formula V compound is condensed with the appropriate hydrazine in a solvent (e.g. typically $(C_1-C_4)$alcohols) at a temperature of 50° C. to 100° C. for 2 to 8 hours at ambient pressures.

Alternatively, according to Reaction Scheme II Formula I compounds, wherein X is N and $R_1$, $R_2$ and $R_3$ are as defined above (i.e. Formula VI compounds), may be prepared from the appropriate Formula VII compound wherein $R_1$ and $R_2$ are as defined above by amination with the appropriate amine.

Typically the Formula VII compound is heated in an anhydrous solvent at temperatures of 50° C. to 150° C. with the appropriate amine for 2 to 8 hours. Typically an excess of the appropriate amine or an equivalent of the appropriate amine and an excess of a trialkylamine (used to react with a halo acid that is liberated in the reaction) is used.

The Formula VII compounds wherein $R_1$ and $R_2$ are as defined above, may be prepared by halogenation of the appropriate Formula VIII compounds wherein $R_1$ and $R_2$ are as defined above. Generally the Formula VIII compound is heated neat with an appropriate halogenating agent such as thionyl chloride, oxalyl chloride, or phosphorous oxytrichloride at temperatures of 50° C. to 150° C. for 2 to 8 hours.

According to Reaction Scheme II Formula VIII compounds wherein $R_1$ and $R_2$ are as defined above may be prepared by cyclization of the appropriate Formula IX compound wherein $R_1$ and $R_2$ are as defined above according to the method described above for cyclization of Formula IV compounds into Formula III compounds.

According to Reaction Scheme II Formula IX compounds wherein $R_1$ and $R_2$ are as defined may be prepared by hydrolysis of the appropriate Formula IV compound wherein $R_1$ and $R_2$ are as defined above.

The above hydrolysis should be controlled such that it stops at the intermediate amide. Typically the Formula IV compound is maintained at a temperature of about 0° C. to 20° C. during addition of an acid (e.g., sulfuric) to control the exotherm. Subsequent to addition of the acid the temperature is raised to about 40° C. to 100° C. for about 2 to about 8 hours.

According to Reaction Scheme III Formula XXIII or XX compounds (i.e., Formula I compounds wherein X is C($R_4$)) may be prepared for example, by starting with the appropriate Formula XVIII compound.

The Formula XXIII compounds wherein $R_1$, $R_2$ and $R_3$ are as described above, X is C($R_4$) and $R_4$ is phenyl, halophenyl, alkoxy $(C_1-C_4)$phenyl, alkyl$(C_1-C_4)$phenyl or perhaloalkyl$(C_1-C_4)$phenyl may be prepared from the appropriate Formula XVIII compound, wherein $R_1$ and $R_2$ are as defined above.

The Formula XVIII compound (prepared by reaction of β-keto-cyano compounds and hydrazine derivatives in lower alcohol solvents and reflux temperature) is reacted with the appropriate Formula XXV compound in a lower alcohol solvent at reflux. Alternatively the reaction is performed neat at a temperature of about 200° C. to about 275° C. The resulting Formula XXI compound may be halogenated to prepare the corresponding Formula XXII compound as described for the conversion of Formula VIII compounds to Formula VII compounds above (see Reaction Scheme II). The resulting Formula XXII compound may be aminated to prepare the corresponding Formula XXIII compound as described for the conversion of the Formula VII compounds to Formula VI compounds above (see Reaction Scheme II) to prepare the corresponding Formula XXIII compound.

For those Formula XX compounds, wherein $R_4$ is H and $R_1$, $R_2$ and $R_3$ are as defined above, the Formula XXIII compound is saponified using standard conditions to form the Formula XXIV acid. Exemplary standard conditions are excess aqueous alkane metal base with a water soluble cosolvent at a temperature of ambient to reflux for 1 to 24 hours.

The Formula XXIV acid is heated without solvent for 1 to 24 hours at 180° C. to 250° C. to provide the desired Formula XX compound.

Other Formula I compounds may be prepared by conventional methods from Formula XXIV acids by combination with appropriate alcohols, amines etc.

According to Reaction Scheme III the Formula XIX compounds (i.e., Formula I compounds wherein X is C(C≡N)) wherein $R_1$ and $R_2$ are as defined above may be prepared from the appropriate Formula XVIII compound wherein $R_1$ and $R_2$ are defined above by cyclization of the appropriate Formula XVIII (wherein $R_1$ and $R_2$ are as defined above) compound with ethoxy methylene malonitrile. Generally, the Formula XVIII compound is reacted with ethoxy methylene malonitrile in a lower alcohol solvent at reflux under nitrogen.

The preparation of the Formula XVIII compound is as described above.

The starting materials for the above described reaction schemes (e.g. Formula V compounds, Formula XVIII compounds, Formula XXV compounds, acid halides, amines, hydrazines, prodrug residues) can be synthesized by those skilled in the art starting from common chemical reagents using conventional methods of organic synthesis and in light of this specification.

Some of the preparation methods described herein will require protection of remote functionality (e.g., amine). The need for these protecting groups will vary depending on the nature of the remote functionality and the conditions of the preparation methods. This need is readily determined by one skilled in the art. For a general description of protecting groups (e.g., halo$(C_1-C_4)$alkyl, $(C_1-C_4)$alkoxymethyl, arylmethyl and tri$(C_1-C_4)$alkylsilyl) and their use, see T. W. Greene, *Protective Groups in Organic Synthesis,* John Wiley & Sons, New York, 1991.

Some of the compounds of this invention are basic and form salts with anions. Others are acidic and form salts with cations. All such salts are within the scope of this invention and can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers (e.g., Formula VI compound where $R^2$ or $R^3$ contain chiral mixture as described) can be separated by converting the enantiomeric mixture into a diasteromeric mixture by reaction with an appropriate optically active compound (e.g., t-boc-tryptophan or ephedrine), separating the diastereomers and converting (e.g., hydrolyzing) the individual diastereomers to the corresponding pure enantiomers. All such isomers, including diastereomers and enantiomers are considered as part of this invention.

In addition, when the compounds of this invention form hydrates or solvates they are also within the scope of the invention.

The prodrugs (e.g., acyl) of the present compounds (e.g., amino moieties) may be prepared using conventional methods of organic synthesis for example by acylation of the amine with the appropriate acid halide/anhydride in the presence of an organic amine base (e.g. pyridine, $Et_3N$).

The compounds of this invention are all readily adapted to therapeutic use as tyrosine kinase inhibitors for the treatment of tyrosine kinase dependent diseases/conditions in mammals (e.g., human). Tyrosine kinase dependent diseases or conditions refers to hyperproliferative disorders which are initiated/maintained by aberrant tyrosine kinase enzyme activity. Examples include psoriasis, cancer, immunoregulation (graft rejection), atherosclerosis, angiogenesis (e.g., tumor growth, diabetic retinopathy), etc.

The compounds of this invention are particularly useful in the treatment of resistance to transplantation and autoimmune diseases such as rheumatoid arthritis or psoriasis. In the treatment of resistance to transplantation, a compound of this invention may be used either prophylactically or in response to an adverse reaction by the human subject to a transplanted organ or tissue. When used prophylactically, a compound of this invention is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of this invention is administered directly to the patient in order to treat resistance to transplantation after outward signs of the resistance have been manifested.

For use in the treatment of tyrosine kinase dependent diseases/conditions (e.g., resistance to transplantation and autoimmune diseases (e.g., rheumatoid arthritis or psoriasis)) in a mammal, including a human, a compound of this invention may be formulated into a suitable pharmaceutical composition containing a tyrosine kinase disease or condition treating effective amount. In general, about 0.05 mg/kg per day to about 30 mg/kg per day per body weight of the mammal, in single or multiple daily doses, is the amount of drug administered. A more preferred range is 0.10 mg/kg per day to about 20 mg/kg per day per body weight of the mammal, although in particular cases, at the discretion of the attending physician, doses outside the broader range may be required. In any event the amount and timing of compound(s) administered will, of course, be dependent on the subject being treated, on the severity of the affliction, on the manner of administration and on the judgment of the prescribing physician.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. Topical administration may also be indicated, for example, where the patient is suffering from a skin disease such as psoriasis or whenever the medication is best applied to the surface of a tissue or organ as determined by the attending physician.

The compounds of the present invention are generally administered in the form of a pharmaceutical composition comprising at least one of the compounds of this invention together with a pharmaceutically acceptable vehicle or diluent. Thus, the compounds can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitable buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the signs of the subject being treated, i.e., a tyrosine kinase dependent disease.

The utility of the compounds of the present invention as medical agents in the treatment of resistance to transplantation and autoimmune diseases such as rheumatoid arthritis or psoriasis is demonstrated by the activity of the compounds of this invention in the biological assay described below. This biological assay also provides a means whereby the activities of the compounds of the present invention can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to generate an immune response in vitro which is measured via $^3$H-thymidine uptake. This assay uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 tissue culture (Sigma, Inc.) enriched with: 0.5% MEM non-essential amino acids (100×) solution, 1% L-glutamine (200 mM), 1% MEM vitamins (100×), 1% penicillin streptomycin solution (10,000 units/mL) and 15% heat-inactivated human AB serum (NABI). The cells are counted and the concentration is adjusted to 5×10$^5$ cells/mL. The solution is then transferred to round bottom 96 well plates in 100 μL/well quantities. These plates contain the responder cells.

The stimulator cells are prepared by pooling the mononuclear cells collected from several different individuals. The cells are suspended in 90% human AB serum and 10% DMSO such that the cell count is 2×10$^7$ cells/mL. The cells are stored in liquid nitrogen. For an MLR, the viable cells are diluted to 5×10$^5$ cells/mL, and 100 μL/well is added to the plates containing the responder cells. To each well, containing a mixture of responder cells and stimulator cells, is added 50 μL of compound solution. Triplicate wells are run for each dose. The plates are incubated at 37° C. under an atmosphere of 5% CO$_2$ and are humidified for five days. To each well is added 1 μCi of $^3$H-thymidine and incubation is continued for another eighteen hours. The cells are harvested using a Wallac Inc. (Gaithersburg, Md.) Beta Plate system. The percent inhibition of stimulated control is obtained using the following equation:

$$\% \text{ Inhibition} = \left[1 - \left(\frac{\text{avg. cpm of drug}}{\text{avg. cpm of stimulated control}}\right)\right] \times 100$$

The abbreviation cpm is defined as counts per minute.

Activity in the MLR screen recited above is indicative of usefulness of the active compound in the treatment of resistance to transplantation and autoimmune diseases such as rheumatoid arthritis and psoriasis.

The utility of the compounds of the present invention as medical agents in the treatment of tyrosine kinase dependent diseases is further demonstrated by the activity of the compounds of this invention in the biological screens described below. The biological screens also provide a means whereby the activities of the compounds of this invention can be compared with the activities of other known compounds. The results of these comparisons are useful for determining dosage levels in mammals, including man, for the treatment of tyrosine kinase dependent diseases such as cancer, atherosclerosis, antiangiogenesis, graft rejection, rheumatoid arthritis or psoriasis.

The in vitro tyrosine kinase inhibitor activity of the present compounds may be demonstrated by methods based on standard procedures. In one method the enzyme pp60src, which is a tyrosine-specific phosphokinase (tyrosine kinase) associated with the inner surface of the plasma membrane, is purified from Rous sarcoma virus-transformed rat cells. In the basis assay the enzyme is incubated with the substrate, 6 mg/mL val5 angiotensin II (Sigma Inc., St. Louis, Mo.), and 20 μM gamma-32p-ATP in a total volume of 25 μl for 25 minutes at 30° C. according to Wong, T. W., Goldberg, A. R., *J. Biol. Chem.*, 259, 8505–8512 (1984). The reaction is terminated by the addition of 45 μl of 5% TCA, incubated on ice for 5 minutes and centrifuged for 1 minute to remove precipitated protein. 35 μl aliquots of the supernatants are applied to phosphocellulose paper circles, which are then washed in 3 changes of 0.5% H$_3$PO$_4$, acetone-rinsed, dried and counted by liquid scintillation. For assaying the compound to be tested is included in the 25 μl incubation mixture; compounds are tested at 10$^{-4}$M, 10$^{-5}$M and 10$^{-6}$M and appropriate solvent controls are included in all assays.

The in vitro tyrosine kinase inhibitor activity of the present compounds may also be demonstrated by a method in which an immune complex kinase assay (ICKA) is used to assess the specificity of tyrosine kinase inhibitors against a panel of Src-family protein tyrosine kinases (PTK).

96-well assay plates are coated with enolase (100 ul) (Sigma Inc.) for the 1 h at 37° C. and then blocked with 300 ul 0.5% BSA. A cell lysate containing the kinase of interest is prepared. The kinase of interest is produced by the baculovirus expression system in cells. The cells are lysed in 0.5% NP-40, 0.02M Tris, 150 mM NaCl and 1% aprotinin. The kinase is immunoprecipitated from the lysate with the appropriate antibody and subsequent incubation with protein-A coated Sepharose (Sigma, Inc., St. Louis, Mo.) beads. The beads are washed four times in a 1:10 bead to wash buffer volume ratio. They are resuspended to their final volume in kinase buffer and then aliquoted with an Eppendorf repeater pipet into appropriate assay wells. (Kinase buffer=25 mM HEPES, 3 mM MnCl2, 0.1 mM Na$_3$VO$_4$). Compounds of this invention and gamma-32P-ATP are then added to assay wells. After the final 20 min incubation, the assay wells are washed with an 1 mM ATP/50 mM EDTA buffer in two 9 sec wash cycles on a Microcell 96 Harvestor (Skatron Instruments, Sterling, Va.).

Scintillant is added to each well and the plate is read on a Micro-Beta Wallac, Inc. (Gaithersburg, Md.) reader. Generally, only alternate rows on an assay plate are used due to the inability of the crosstalk correction program of the Micro-Beta to correct for the high energy beta in adjacent wells. Samples are run in triplicate, averaged and then plotted to determine an IC$_{50}$.

It should be understood that the invention is not limited to the particular embodiments described herein, but that various changes and modifications may be made without departing from the spirit and scope of this novel concept as defined by the claims.

EXAMPLE 1

4-Amino-5,7-diphenylpyrazolo-[3,4-d]pyrimidine

A mixture of 5-amino-4-cyano-1,3-diphenylpyrazole (0.94 g, 3.62 mmol), formamide (5.5 mL), formic acid (0.7 mL) and dimethylformamide (2 mL) were heated at 180° C. for 6 hours. The reaction mixture was allowed to cool and diluted with water. The resulting solids were filtered off and recrystallized from ethanol to afford 0.75 g of the title compound; m.p. 244°–246° C. Anal. calcd. for $C_{17}H_{13}N_5 \cdot 0.1\ H_2O$: C, 70.62; H, 4.60; N, 24.22. Found: C, 70.49; H, 4.40; N, 24.19.

The following pyrazolo[3,4-d]pyrimidines (Examples 2–45) were prepared using procedures analogous to that detailed above:

EXAMPLE 2

4-Amino-7-(4'-methoxyphenyl)-5-phenylpyrazolo[3,4-d]pyrimidine m.p. 204°–206° C. ($CHCl_3$/hexanes). Anal. calcd. for $C_{18}H_{15}N_5O \cdot 0.25\ H_2O$: C, 67.17; H, 4.85; N, 21.76. Found: C, 67.50; H, 4.62; N, 21.58.

EXAMPLE 3

4-Amino-7-(3',4'-dichlorophenyl)-5-phenylpyrazolo-[3,4-d]pyrimidine m.p. 306°–307° C. (DMF/MeOH). Anal. calcd. for $C_{17}H_{11}Cl_2N_5 \cdot 0.25\ H_2O$: C, 56.60; H, 3.21; N, 19.42. Found: C, 56.76; H, 2.97; N, 19.24.

EXAMPLE 4

4-Amino-5-phenyl-7-(2'-pyridyl)-pyrazolo[3,4-d]-pyrimidine m.p. 267°–269° C. (DMF/MeOH).

EXAMPLE 5

4-Amino-7-(4'-nitrophenyl)-5-phenylpyrazolo[3,4-d]pyrimidine m.p. 348°–349° C. (DMF/MeOH). Anal. calcd. for $C_{17}H_{12}N_6O_2$: C, 61.43; H, 3.64; N, 25.29. Found: C, 61.16; H, 3.37; N, 24.90.

EXAMPLE 6

4-Amino-5-(4'-methylphenyl)-7-phenylpyrazolo[3,4-d]pyrimidine m.p. 248°–250° C. (EtOH/$H_2O$). Anal. calcd. for $C_{18}H_{15}N_5 \cdot 0.5\ H_2O$: C, 69.65; H, 4.87; N, 22.57. Found: C, 69.54; H, 4.53; N, 22.27.

EXAMPLE 7

4-Amino-5-(4'-methylphenyl)-pyrazolo[3,4-d]pyrimidine m.p. >300° C. (MeOH). Anal. calcd. for $C_{12}H_{11}N_5 \cdot 0.1\ H_2O$: C, 63.47; H, 4.97; N, 30.85. Found: C, 63.44; H, 4.71; N, 30.59.

EXAMPLE 8

4-Amino-7-benzyl-5-(4'-methylphenyl)-pyrazolo[3,4-d]pyrimidine m.p. 195°–196° C. (EtOH/$H_2O$). Anal. calcd. for $C_{19}H_{17}N_5$: C, 72.36; H, 5.43; N, 22.21. Found: C, 72.16; H, 5.10; N, 22.04.

EXAMPLE 9

4-Amino-7-t-butyl-5-(4'-methylphenyl)-pyrazolo[3,4-d]pyrimidine m.p. 203°–204° C. (EtOH). Anal. calcd. for $C_{16}H_{19}N_5 \cdot 0.25\ H_2O$: C, 67.22; H, 6.87; N, 24.50. Found: C, 67.46; H, 6.59; N, 24.04.

EXAMPLE 10

4-Amino-5-(4'-methylphenyl)-7-(2"-pyridyl)-pyrazolo[3,4-d]pyrimidine m.p. 266°–269° C. (MeOH). Anal. calcd. for $C_{17}H_{14}N_6$: C, 67.53; H, 4.67; N, 27.80. Found: 67.21; H, 4.50; N, 27.75.

EXAMPLE 11

4-Amino-7-(1'-naphthyl)-5-phenylpyrazolo[3,4-d]pyrimidine m.p. 233°–235° C. (DMF/hexanes). Anal. calcd. for $C_{21}H_{15}N_5$: C, 74.75; H, 4.48; N, 20.76. Found: H, 74.36; N, 4.29; N, 20.14.

EXAMPLE 12

4-Amino-7-(2'-methylphenyl)-5-phenylpyrazolo[3,4-d]pyrimidine m.p. 159°–161° C. ($CHCl_3$/hexanes).

EXAMPLE 13

4-Amino-5-benzyl-7-phenylpyrazolo[3,4-d]pyrimidine m.p. 167°–168° C. (EtOH). Anal. calcd. for $C_{18}H_{15}N_5$: C, 71.74; H, 5.02; N, 23.24. Found: C, 71.47; H, 4.90; N, 22.93.

EXAMPLE 14

4-Amino-5-t-butyl-7-phenylpyrazolo[3,4-d]pyrimidine m.p. 174°–176° C. (EtOH/$H_2O$). Anal. calcd. for $C_{15}H_{17}N_5$: C, 67.39; H, 6.41; N, 26.20. Found: C, 67.23; H, 6.00; N, 25.86.

EXAMPLE 15

4-Amino-5,7-di-t-butylpyrazolo[3,4-d]pyrimidine m.p. 158°–161° C. (EtOH/$H_2O$). Anal. calcd. for $C_{13}H_{21}N_5$: C, 63.12; H, 8.56; N, 28.32. Found: C, 63.14; H, 8.54; N, 28.16.

EXAMPLE 16

4-Amino-5-benzyl-7-t-butylpyrazolo[3,4-d]pyrimidine m.p. 138°–140° C. (EtOH/$H_2O$). Anal. calcd. for $C_{16}H_{19}N_5 \cdot 0.2\ H_2O$: C, 67.44; H, 6.86; N, 24.58. Found: C, 67.71; H, 6.91; N, 24.37.

EXAMPLE 17

4-Amino-5-(4-methylphenyl)-7-cycloheptyl-pyrazolo[3,4-d]pyrimidine m.p. 174°–175° C.

EXAMPLE 18

4-Amino-5-(4-methylphenyl)-7-(2-hydroxybutyl)-pyrazolo[3,4-d]-pyrimidine m.p. 134°–135° C.

EXAMPLE 19

4-Amino-5-(4-methylphenyl)-7-(4-hydroxybutyroyl)-pyrazolo[3,4-d]-pyrimidine m.p. 294°–295° C.

EXAMPLE 20

4-Amino-5-(3-fluoro-4-methylphenyl)-7-(2-fluorophenyl)-pyrazolo-[3,4-d]pyrimidine m.p. 202°–204° C.

EXAMPLE 21

4-Amino-5-(4-methylphenyl)-7-butyl-pyrazolo-[3,4-d]-pyrimidine m.p. 152°–153° C.

EXAMPLE 22

4-Amino-5-(4-trifluoromethylphenyl)-7-t-butyl-pyrazolo[3,4-d]-pyrimidine m.p. 168°–170° C.

EXAMPLE 23

4-Amino-5-(4-methylphenyl)-7-cyclohexyl-pyrazolo[3,4-d]-pyrimidine m.p. 179°–180° C.

EXAMPLE 24

4-Amino-5-(4-fluorophenyl)-7-(2-ethylacetyl)-pyrazolo-[3,4-d]-pyrimidine m.p. 186°–188° C.

EXAMPLE 25

4-Amino-5-(4-trifluoromethylphenyl)-7-(benzyl)-pyrazolo-[3,4-d]pyrimidine m.p. 185°–187° C.

EXAMPLE 26

4-Amino-5-(4-methylphenyl)-7-(2-ethylacetyl)-pyrazolo-[3,4-d ]-pyrimidine m.p. 164°–165° C.

EXAMPLE 27

4-Amino-5-(4-trifluoromethylphenyl)-7-(4-methoxyphenyl)-pyrazolo-[3,4-d]-pyrimidine m.p. 230°–232° C.

EXAMPLE 28

4-Amino-5-(trifluoromethylphenyl)-7-phenyl-pyrazolo-[3,4-d]-pyrimidine m.p. 265°–267° C.

EXAMPLE 29

4-Amino-5-(4-chlorophenyl)-7-(2-chlorophenyl)-pyrazolo-[3,4-d]-pyrimidine m.p. 196°–197° C.

EXAMPLE 30

4-Amino-5-(4-chlorophenyl)-7-(4-methylphenyl)-pyrazolo-[3,4-d]-pyrimidine m.p. 259°–260° C.

EXAMPLE 31

4-Amino-5-(4-chlorophenyl)-7-t-butyl-pyrazolo-[3,4-d]-pyrimidine m.p. 192°–193° C.

EXAMPLE 32

4-Amino-5-(4-chlorophenyl)-7-(2-fluorophenyl)-pyrazolo-[3,4-d]-pyrimidine m.p. 213°–214° C.

EXAMPLE 33

4-Amino-5-(4-chlorophenyl)-7-(3-methoxyphenyl)-pyrazolo-[3,4-d]-pyrimidine m.p. 214°–215° C.

EXAMPLE 34

4-Amino-5-(4-methylphenyl)-7-(2,6-dichlorophenyl)-pyrazolo-[3,4-d]-pyrimidine m.p. 245°–246° C.

EXAMPLE 35

4-Amino-5-(4-methylphenyl)-7-(2-(4,5-dihydrolimidazole)-pyrazolo-[3,4-d]-pyrimidine m.p. 295°–297° C. (decomposition).

EXAMPLE 36

4-Amino-5-(4-methylphenyl)-7-(3-trifluoromethylphenyl)-pyrazolo-[3,4-d]-pyrimidine m.p. 219°–220° C.

EXAMPLE 37

4-Amino-5-(4-methylphenyl)-7-(4-isopropylphenyl)-pyrazolo-[3,4-d]-pyrimidine m.p. 164°–165° C.

EXAMPLE 38

4-Amino-5-(4-methylphenyl)-7-(4-t-butylphenyl)-pyrazolo-[3,4-d]-pyrimidine m.p. 185°–186° C.

EXAMPLE 39

4-Amino-5-(4-methylphenyl)-7-(2,4-difluorophenyl)-pyrazolo-[3,4-d]pyrimidine m.p. 203°–204° C.

EXAMPLE 40

4-Amino-5-(4-methylphenyl)-7-(2,5-difluorophenyl)-pyrazolo-[3,4-d]pyrimidine m.p. 215°–216° C.

EXAMPLE 41

4-Amino-5-(4-methylphenyl)-7-(2-methoxyphenyl)-pyrazolo-[3,4-d]pyrimidine m.p. 191°–192° C.

EXAMPLE 42

4-Amino-5-(4-methylphenyl)-7-(4-methoxyphenyl)-pyrazolo-[3,4-d]pyrimidine m.p. 199°–200° C.

EXAMPLE 43

4-Amino-5-phenyl-7-t-butyl-pyrazolo-[3,4-d]-pyrimidine m.p. 174°–175° C.

EXAMPLE 44

4-Amino-5-(4-methylphenyl)-7-(2-methylphenyl)-pyrazolo-[3,4-d]pyrimidine m.p. 179°–180° C.

EXAMPLE 45

4-Amino-5-(4-methylphenyl)-7-(4-chlorophenyl)-pyrazolo-[3,4-d]-pyrimidine m.p. 276°–277° C.

EXAMPLE 46

5-(4'-Methylphenyl)-7-phenyl-4-(3"-(N-morpholino)-propylamino) pyrazolo[3,4-d]pyrimidine A solution of 4-chloro-5-(4'-methylphenyl)-7-phenylpyrazolo[3,4-d]pyrimidine (0.4 g, 1.2 mmol) and 3-(N-morpholino)-propylamine (0.5 mL, 3.7 mmol) in ethanol (8 mL) was refluxed for 3 hours. The ethanol was evaporated in vacuo, the residue dissolved in EtOAc, washed with water, dried ($Na_2SO_4$), filtered and concentrated in vacuo. The solid residue was recrystallized from MeOH to afford 0.3 g of the title compound; m.p. 140°–141° C. Anal. calcd. for $C_{25}H_{28}N_6O$: C, 70.07; H, 6.59; N, 19.61. Found: C, 70.09; H, 6.64; N, 19.63.

EXAMPLE 47

5-(4'-Methylphenyl)-7-phenyl-4-N-(ethylglycinate)-pyrazolo[3,4-d]pyrimidine

A solution of 4-chloro-5-(4'-methylphenyl)-7-phenylpyrazolo[3,4-d]pyrimidine (0.8 g, 2.5 mmol) ethyl glycinatehydrochloride (1.0 g, 7.5 mmol) and triethylamine (1.1 mL, 7.6 mmol) in ethanol (16 mL) was refluxed for 3 hours. The ethanol was evaporated in vacuo, the residue dissolved in EtOAc, washed with water, dried ($Na_2SO_4$), filtered and concentrated in vacuo. The solid residue was recrystallized from MeOH to afford 0.9 g of the title compound; m.p. 165°–166° C. Anal. calcd. for $C_{22}H_{21}N_5O_2$: C, 68.20; H, 5.46; N, 18.08. Found: C, 68.07; H, 5.44; N, 18.12.

EXAMPLE 48

5-(4'-Methylphenyl)-7-phenyl-4-N-glycinylpyrazolo[3,4-d]pyrimidine

A solution of 5-(4'-methylphenyl)-7-phenyl-4-N-(ethyl glycinate)pyrazolo[3,4-d]pyrimidine (0.39 g, 1.0 mmol) and potassium hydroxide (0.1 g) in ethanol (6 mL) was refluxed for 30 minutes. After cooling, water was added and the pH of the reaction mixture was adjusted to 4. The solids were extracted into EtOAc and the organic phase was washed with water, brine and dried ($Na_2SO_4$). Concentration in vacuo provided a solid mass which was recrystallized from ethanol to afford 0.28 g of the title compound; m.p. 238°–241° C. Anal. calcd. for $C_{20}H_{17}N_5O_2$: C, 66.84; H, 4.77; N, 19.49. Found: C, 66.54; H, 4.42; N, 19.22.

EXAMPLE 49

4-Amino-7-benzoyl-5-(4'-methylphenyl)-pyrazolo[3,4-d]pyrimidine

To a stirred solution of 4-amino-5-(4'-methylphenyl)pyrazolo[3,4-d]pyrimidine (0.40 g, 1.77 mmol) in pyridine (9 mL) was added benzoyl chloride (0.25 g, 1.77 mmol) dropwise. After 45 minutes, the pyridine was removed in vacuo and the resulting solids were washed with water and EtOH to afford 0.28 g of the title compound; m.p. 297°–300° C. Anal. calcd. for $C_{19}H_{15}N_5 \cdot 0.75\ H_2O$: C, 66.55; H, 4.85; N, 20.42. Found: C, 6.43; H, 4.69; N, 19.77.

EXAMPLE 50

5-Cyano-4-amino-3-(4-chlorophenyl)-1-t-butylpyrazolo-(3,4-b)-pyridine

To a stirred solution of the compound from preparation V (0.3 g) dissolved in ethanol (4 mL) was added ethoxy methylene malononitrile (0.18 g). The mixture was refluxed under nitrogen for 24 hours, cooled to room temperature and the solvent removed in vacuo. The residue was chromatographed over silica gel with 25% ethylacetate in hexane to afford yellow crystals 30 mg; m.p. 213°–215° C.

EXAMPLE 51

3-(4-Chlorophenyl)-4-amino-1-tertbutyl-1H-pyrazolo[3,4-b]pyridine-5-carboxylic acid ethyl ester A solution of 0.5 g (1.27 mmol) of the product of Preparation Y in 10 mL of ethanol saturated with ammonia gas was heated in a thick walled sealed glass tub at 125°–130° C. for 60 hours. The cooled reaction mixture was concentrated and the residue was triturated with ether and filtered. The filtrate was dried (MgSO$_4$), filtered, and concentrated to leave 0.26 g of crude amine as a yellow solid. The solid was purified on silica gel column (10% Et$_2$O/Hex) to provide 0.16 g pure white solid.

$^1$H NMR (CDCl$_3$) δ1.41 (t, 3H), 1.86 (s, 9H), 4.35 (q, 2H), 7.48 (d, 2H), 7.62 (d, 2H), 8.88 (s, 1H)

EXAMPLE 52

3-(4-Chlorophenyl)-4-amino-1-tertbutyl-1H-pyrazolo[3,4-b]pyridine

A 1.21 g (4.61 mmol) portion of the compound from Preparation Z was heated at 180°–185° C. under nitrogen until gas evolution stopped. The product sublimed on the sides of the reaction flask. The white crystals were removed. mp—158.5°–165° C.

1$^1$H MNR (CDCl$_3$) δ1.88 (s, 9H), 4.55 (bs, 2H), 6.25 (d, 1H), 7.49 (d, 2H), 7.68 (d, 2H), 8.16 (d, 1 H)

PREPARATION A 1,1-Dicyano-2-methoxy-2-(phenyl)ethylene

The title compound was prepared according to the procedure of Dornow, A.; Schleese, E., *Chem. Ber.* 1958, 91, 1830.

PREPARATION B 1,1-Dicyano-2-methoxy-2-(4'-methylphenyl)ethylene

The title compound was prepared according to the procedure of Southwick, P. L.; Dhawan, B., *J. Hetero. Chem.* 1975, 12, 1199.

The following 5-amino-4-cyanopyrazoles (Preparations C–R) were prepared from the appropriate 1,1-dicyano-2-methoxy(ethoxy)ethylene and hydrazine using the general procedure described in Southwick, P. L.; Dhawan, B., *J. Hetero. Chem.* 1975, 12, 1199.

PREPARATION C

5-Amino-4-cyano-1,3-diphenylpyrazole m.p. 169° C. (EtOH; lit. m.p. 172°–173° C.; Dickinson, C. L.; Williams, J. K.; McKusick, *J. Org. Chem.* 1964, 29, 1915).

PREPARATION D

5-Amino-4-cyano-1-(4'-methoxyphenyl)-3-phenylpyrazole

PREPARATION E

5-Amino-4-cyano-1-(3',4'-dichlorophenyl)-3-phenylpyrazole m.p. 197.5°–198° C.

PREPARATION F

5-Amino-4-cyano-3-phenyl-1-(2'-pyridyl)pyrazole m.p. 243.5°–245.5° C.

PREPARATION G

5-Amino-4-cyanol-(4'-nitrophenyl)-3-phenylpyrazole m.p. 257.5°–258° C.

PREPARATION H

5-Amino-4-cyano-3-(4'-methylphenyl)-1-phenylpyrazole m.p. 186°–188° C. (EtOH). Anal. calcd. for C$_{11}$H$_{14}$N$_4$.0.2 H$_2$O: C, 73.47; H, 5.22; N, 20.16, Found: C, 73.75; H, 4.83; N, 19.84.

PREPARATION I

5-Amino-4-cyano-3-(4'-methylphenyl)pyrazole m.p. 173°–178° C. (EtOH/H$_2$O).

PREPARATION J

5-Amino-1-benzyl-4-cyano-3-(4'-methylphenyl)pyrazole m.p. 162°–163° C. (EtOH/H$_2$O). Anal. calcd. for C$_{18}$H$_{16}$N$_4$: C, 74.97; H, 5.59; N, 19.43. Found: C, 74.71; H, 5.34; N, 19.34.

PREPARATION K

5-Amino-1-t-butyl-4-cyano-3-(4'-methylphenyl)pyrazole m.p. 174°–176° C. (EtOH/H$_2$O). Anal. calcd. for C$_{15}$H$_{18}$N$_4$: C, 70.84; H, 7.13; N, 22.03. Found: C, 70.69; H, 7.13; N, 21.99.

PREPARATION L

5-Amino-4-cyano-3-(4'-methylphenyl)-1-(2''-pyridyl)pyrazole m.p. 209°–211° C. (EtOH/H$_2$O). Anal. calcd. for C$_{16}$H$_{13}$N$_5$.0.1 H$_2$O: C, 69.35; H, 4.80; N, 25.28. Found: C, 69.28; H, 4.51; N, 25.44.

PREPARATION M

5-Amino-3-benzyl-4-cyanopyrazole m.p. 183°–185° C. (MeOH/H$_2$O). Anal. calcd. for C$_{17}$H$_{14}$N$_4$: C, 74.43; H, 5.14, N, 20.43. Found: C, 74.53; H, 4.83; N, 20.33.

PREPARATION N

5-Amino-3-t-butyl-4-cyano-1-phenylpyrazole oil.

PREPARATION O

5-Amino-4-cyano-1,3-di-t-butylpyrazole m.p. 78°–80° C. (MeOH/H$_2$O). Anal. calcd. for C$_{12}$H$_{20}$N$_4$.0.15 H$_2$O: C, 64.53; H, 9.18; N, 25.09. Found: C, 64.71; H, 9.12; N, 25.03.

PREPARATION P

5-Amino-3-benzyl-1-t-butyl.-4-cyanopyrazole m.p. 112°–114° C. (MeOH/H$_2$O). Anal. calcd. for C$_{15}$H$_{18}$N$_4$: C, 70.84; H, 7.13; N, 22.03. Found: C, 70.59; H, 7.08; N, 21.72.

PREPARATION Q

5-Amino-4-cyano-1-(1'-naphthyl)-3-phenylpyrazole m.p. 202°–203° C. (CHCl$_3$/hexanes).

PREPARATION R

5-Amino-4-cyano-1-(2'-methylphenyl)-3-phenylpyrazole m.p. 119°–121° C. (CHCl$_3$/hexanes).

PREPARATION S

5-Amino-3-(4'-methylphenyl)-1-phenyl-4-pyrazolecarboxamide

While maintaining an internal reaction temperature of 10°–15° C., 5-amino-4-cyano-3-(4'-methylphenyl)-1-phenylpyrazole (3.4 g, 12 mmol) was added in a portionwise manner to concentrated sulfuric acid (15 mL). After the addition was complete, the reaction mixture was heated at 50° C. for 4 hours. The reaction was cooled, poured over ice, neutralized with concentrated ammonium hydroxide and extracted with EtOAc. The organic layer was washed with water, dried (Na$_2$SO$_4$), filtered and concentrated in vacuo. The resulting solids were recrystallized from MeOH/H$_2$O to afford 3.0 g of the title compound; m.p. 190°–191° C.

PREPARATION T 5-(4'-Methylphenyl)-7-phenylpyrazolo[3,4-d]-pyrimidin-4-one

A solution of 5-amino-3-(4'-methylphenyl)-1-phenyl-4-pyrazolecarboxamide (2.9 g, 9.9 mmol) in formamide (5 mL) was heated at 190° C. for 8 hours. After cooling the solids were filtered, washed with water and dried to afford 2.7 g of the title compound; m.p. 260°–262° C. (MeOH). Anal. calcd. for C$_{18}$H$_{14}$N$_4$O: C, 71.50; H, 4.67; N, 18.53. Found: C, 71.09; H, 4.50; N, 18.41.

PREPARATION U

4-Chloro-5-(4'-methylphenyl)-7-phenylpyrazolo[3,4-d]pyrimidine

A solution of 5-(4'-methylphenyl)-7-phenylpyrazole[3,4-d]pyrimidin-4-one (4.73 g, 15.6 mmol) in phosphorus oxychloride (25 mL) was refluxed for 2.5 hours. The excess phosphorus oxychloride was removed in vacuo, the residue was poured over ice and extracted with chloroform. The organic layer was washed with water, dried (Na$_2$SO$_4$) and concentrated in vacuo to afford 4.9 g of the title compound; m.p. 177°–179° C. (heptane/toluene). Anal. calcd. for C$_{18}$H$_{13}$ClN$_4$: C, 67.89; H, 4.08; N, 17.48. Found: C, 67.99; H, 3.95; N, 17.21.

PREPARATION V 1-t-Butyl-3-(4-chlorophenyl)-5-amino-(1,2)-pyrazole

To a stirred solution of 4-chlorobenzoyl acetonitrile (Aldrich) (10 g) in 200 mL of isopropanol was added t-butyl hydrazone.HCl (8.32 g) and triethyl amine (15.5 mL). The mixture was refluxed for 6 hours under N$_2$, cooled to room temperature and the solvent removed under vacuum. The solid was dissolved in EtOAc (200 mL) and washed with water, brine and then dried over K$_2$CO$_5$. The organic layer was filtered, the solvent removed under vacuum and the residue chromatographed over silica gel with 30% ethylacetate in hexane to afford 2.11 g of a yellow solid; m.p. 108°–113° C.

PREPARATION W

[[(3-(4-Chlorophenyl)-1-t-butyl-5-pyrazolyl)-amino]methylene]malonic acid diethyl ester A stirred mixture of 17.60 g (70.4 mmol) of the product from Preparation V and 15.24 g (70.4 mmol) of diethyl (ethoxymethylene)malonate was heated at 120° C. for 4 hours under vacuum conc. in vacuo to give 29.56 g (70.4 mmol) of intermediate enamine as an orange oil which was used without further purification.

$^1$H NMR (CDCl$_3$) δ1.31 (t, 3H), 1.4 (t, 3H), 1.62 (s, 9H) 4.28 (q, 2H), 4.33 (q 2H), 6.39 (s, 1H), 7.36 (d, 2H), 7.72 (d, 2H), 8.16 (d, 1H).

PREPARATION X 3-(4-Chlorophenyl)-4-hydroxy-1-tertbutyl-1H-pyrazolo[3,4-b]-pyridine-5-carboxylic acid ethyl ester A solution of 29.56 g (30.4 mmol) of enamine from Preparation W in 57 mL of diphenyl ether was heated at 235°–255° C. under a nitrogen atmosphere for 60 hours. The reaction was cooled and chromatographed on silica gel (hexane→5% EtOAc/Hex) to separate the product 2.07 g, 5.54 mmol.

$^1$H NMR (CDCl$_3$) δ1.46 (t, 3H), 1.87 (s, 9H), 4.49 (q, 2H), 7.44 (d, 2H), 8.06 (d, 2H), 8.89 (s, 1H).

PREPARATION Y

3-(4-Chlorophenyl)-4-chloro-1-tertbutyl-1H-pyrazolo[3,4-b]pyridine-5-carboxylic acid ethyl ester A solution of 2.07 g (5.54 mmol) of the compound from Preparation X and 7 mL of phosphorus oxychloride ($POCl_3$) was refluxed for 3 hours and then concentrated to remove the $POCl_3$. The residue was diluted with water and the resulting mixture was extracted with EtOAc. The combined extracts were dried ($MgSO_4$), filtered, and concentrated to leave 0.5 (23%) of chloro product as an orange solid which was used without further purification.

$^1$H NMR ($CDCl_3$) δ1.45 (t, 3H), 1.88 (s, 9H), 4.47 (q, 2H), 7.45 (d, 2H), 7.63 (d, 2H), 8.98 (s, 1H)

PREPARATION Z

3-(4-Chlorophenyl)-4-amino-1-tertbutyl-1H-pyrazolo[3,4-b]pyridine-5-carboxylic acid A solution of the compound from Example 51 (0.8 mmol) and 0.12 g (3 mmol) of sodium hydroxide in 6 mL of 95% ethanol was warmed at 45°–50° C. for 12 hours and then concentrated. The residue was dissolved in 300 mL of water, filtered, and acidified with acetic acid whereupon a white precipitate formed. The solid was collected, washed with water, and air-dried to give 0.08 g of a white solid.

$^1$H NMR ($CDCl_3$) δ1.87 (s, 9H), 7.49 (d, 2H), 7.63 (d, 2H), 8.94 (s, 1H).

We claim:

1. A compound of Formula I

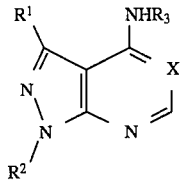

Formula I and the pharmaceutically-acceptable salts and prodrugs thereof wherein X is N;

$R_1$ is phenyl, mono- or di-alkyl ($C_1$–$C_4$)phenyl or furyl;

$R_2$ is mono- or di-halophenyl, mono- or di-alkoxy ($C_1$–$C_4$)phenyl, mono- or di-alkyl ($C_1$–$C_4$)phenyl, perhaloalkyl ($C_1$–$C_4$)phenyl, alkyl ($C_1$–$C_6$), cycloalkyl ($C_1$–$C_7$), pyridyl, naphthyl, pyrrolyl imidazolyl, pyrazolyl, pyridyl, pyrimidinyl, pyrazinyl, pyridazinyl, furyl or thienyl; and $R_3$ is H.

2. A compound as recited in claim 1 wherein $R_1$ is phenyl or alkyl ($C_1$–$C_4$)phenyl; and $R_2$ is cyclohexyl, halophenyl, alkoxy ($C_1$–$C_4$)phenyl, alkyl ($C_1$–$C_4$)phenyl or perhaloalkyl ($C_1$–$C_4$)phenyl.

3. A compound as recited in claim 2 wherein $R_1$ is 4-methylphenyl.

4. A compound as recited in claim 1 wherein $R_1$ is alkyl($C_1$–$C_4$)phenyl; and $R_2$ is t-butyl or cyclohexyl.

5. The compound as recited in claim 4 wherein $R_1$ is 4-methylphenyl; and $R_2$ is cyclohexyl.

6. The compound as recited in claim 4 wherein $R_1$ is 4-methylphenyl; and $R_2$ is t-butyl.

7. A compound as recited in claim 1 wherein $R_1$ is phenyl or alkyl($C_1$–$C_4$)phenyl; and $R_2$ is pyridyl or alkyl($C_1$–$C_6$).

8. A compound as recited in claim 7 wherein $R_1$ is 4-methylphenyl.

9. A compound as recited in claim 7 wherein $R_2$ is 2-pyridyl.

10. A compound as recited in claim 1 wherein $R_1$ is phenyl; and $R_2$ is 3,4-dichlorophenyl, 1-naphthyl, 2-methylphenyl or 4-methoxyphenyl.

11. A pharmaceutical composition which comprises a therapeutically effective amount of a compound of claim 1 in a pharmaceutically acceptable carrier.

12. A pharmaceutical composition which comprises a tyrosine kinase dependent disease/condition treating amount of a compound of claim 1 in a pharmaceutically acceptable carrier.

13. A method for treating a tyrosine kinase dependent disease/condition in a mammal which comprises administering to a mammal suffering from a tyrosine kinase dependent disease/condition a tyrosine kinase dependent disease/condition treating amount of a compound of claim 1.

14. The method as recited in claim 13 wherein the tyrosine kinase dependent disease/condition is cancer, atherosclerosis, angiogenesis, graft rejection, rheumatoid arthritis or psoriasis.

15. The method as recited in claim 14 wherein the tyrosine kinase dependent disease/condition is graft rejection, rheumatoid arthritis or psoriasis.

16. The method as recited in claim 14 wherein the tyrosine kinase dependent disease is cancer, atherosclerosis or angiogenesis.

* * * * *